United States Patent [19]

Presby

[11] 4,362,943
[45] Dec. 7, 1982

[54] METHOD OF MEASURING THE REFRACTIVE INDEX PROFILE AND THE CORE DIAMETER OF OPTICAL FIBERS AND PREFORMS

[75] Inventor: Herman M. Presby, Highland Park, N.J.

[73] Assignee: Bell Telephone Laboratories, Incorporated, Murray Hill, N.J.

[21] Appl. No.: 185,202

[22] Filed: Sep. 8, 1980

[51] Int. Cl.³ .......................................... G01N 21/64
[52] U.S. Cl. ............................... 250/459.1; 250/461.1
[58] Field of Search .................... 250/458, 459, 461 R, 250/571; 350/96.29, 96.3, 96.31; 356/73.1

[56] References Cited

U.S. PATENT DOCUMENTS

| | | | |
|---|---|---|---|
| 3,879,128 | 4/1975 | Presby | 250/571 |
| 4,161,656 | 7/1979 | Marcuse et al. | 250/461 R X |
| 4,181,433 | 1/1980 | Marcuse | 356/73.1 |
| 4,307,296 | 12/1981 | Presby | 250/461 R X |

Primary Examiner—Davis L. Willis
Attorney, Agent, or Firm—S. Sherman

[57] ABSTRACT

Shaping of the refractive index profile of an optical fiber is typically achieved by changing the concentration of an index-modifying dopant within the glassy matrix preform. To measure the profile and the core diameter of the preform, in accordance with the present disclosure, the preform (10) is illuminated with a focused beam of ultraviolet radiation (15) whose beam width (w) is small compared to the preform core diameter (d). This induces a fluorescence along a thin pencil-like region (16) of the preform core whose intensity varies in proportion to the concentration of the dopant. Inasmuch as the latter is proportional to the refractive index, the intensity profile gives the index profile directly. A similar measure can also be made on fibers using microscopes for focusing the uv and observing the induced fluorescence. Use of this technique for controlling the rate at which a fiber is drawn is also described.

6 Claims, 7 Drawing Figures

METHOD OF MEASURING THE REFRACTIVE INDEX PROFILE AND THE CORE DIAMETER OF OPTICAL FIBERS AND PREFORMS

TECHNICAL FIELD

The invention relates to a method of determining the refractive index profile and the core diameter of optical fibers and fiber preforms by measuring the concentration and distribution of index-modifying dopants within the fibers and preforms.

BACKGROUND OF THE INVENTION

In U.S. Pat. No. 3,434,774, it is disclosed that more efficient transmission of optical wave energy along a multimode optical fiber is achieved by grading the refractive index of the fiber core. The degree of transmission efficiency achievable with a particular fiber is determined by how closely the fiber's index profile approaches the optimum distribution. Thus, accurate knowledge of the fiber profile is necessary in order to assess the fiber's transmission properties. Inasmuch as a fiber is a reduced replica of the preform from which it is drawn, the profile information sought can just as readily be obtained by measuring it in the preform. Indeed, there are a number of advantages in doing so. Its larger diameter and shorter length make it easier to handle, and permit easy examination over its entire length. Furthermore, a poor preform can be discarded without having incurred the expense of drawing the fiber only to find that the fiber is useless for its intended purpose.

One technique for examining preforms, using the ultraviolet-fluorescence method, is disclosed in U.S. Pat. No. 4,161,656 by D. Marcuse et al. This method is based upon the discovery that the index-modifying dopants used to grade the index profile can be made to fluoresce when illuminated with ultraviolet radiation. In particular, the intensity of this fluorescence is directly proportional to the dopant concentration which, in turn, is proportional to the refractive index. Accordingly, as taught in the above-cited Marcuse et al patent, the dopant concentration is determined by uniformly illuminating the entire width of the fiber preform with uv light and measuring the distribution of the resulting fluorescence along a direction transverse to the longitudinal axis of the preform. However, because the measured fluorescence includes components contributed from throughout the cross section of the core, mathematical manipulation of the data is necessary in order to extract the desired information. Indeed, as a practical matter, a computer is required for these calculations.

SUMMARY OF THE INVENTION

In accordance with the present invention, the index profile and core diameter of optical fibers and optical fiber preforms can be directly obtained by transversely illuminating the fiber/preform with a focused beam of uv radiation whose beamwidth is at least an order of magnitude smaller than the diameter of the fiber/preform core. Illuminated in this manner, the resulting fluorescence is induced along a thin, cylindrical region of the core. Inasmuch as the measured intensity of the fluorescence is proportional to the dopant concentration, the index profile of the preform can be directly observed by this method. The extent of the fluorescence provides a measure of the core diameter.

It is an advantage of the invention that the desired profile information is readily obtainable using simple, inexpensive measuring equipment. In addition, the technique is nondestructive and can be quickly performed.

DETAILED DESCRIPTION

Figure 1:
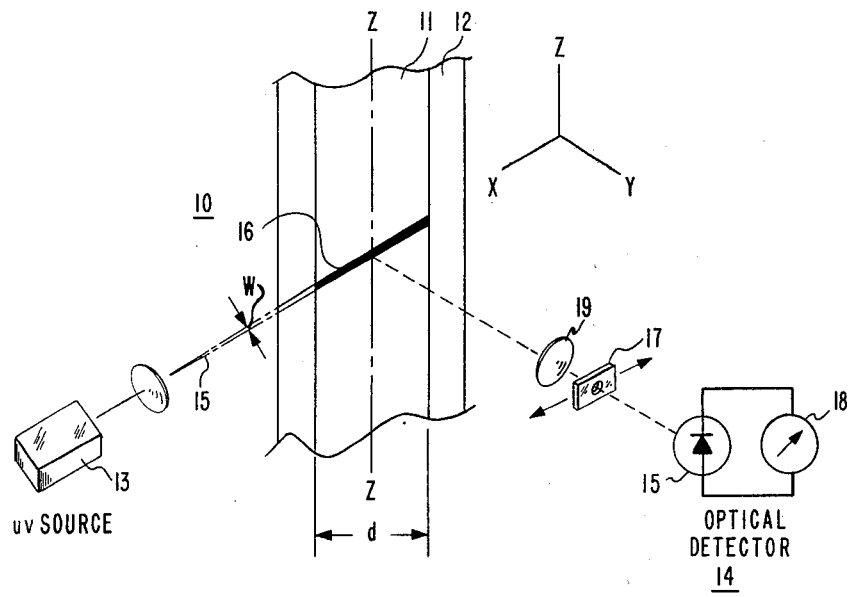
FIG. 1 shows the arrangement of apparatus for practicing the invention.

Referring to the drawings, FIG. 1 shows apparatus, including a uv source 13 and an optical detector 14, for measuring the index profile and the core diameter of an optical fiber/preform 10 comprising an inner core region 11 surrounded by an outer cladding 12. The term "fiber/preform" has been used to indicate that the arrangement of FIG. 1 can be used to measure both fibers and fiber preforms. Accordingly, in the description that follows, the term fiber/preform shall be used to indicate this fact.

As shown in FIG. 1, source 13 directs a focused beam 15 of ultraviolet (uv) radiation through the center of fiber/preform 10 in a direction perpendicular to its longitudinal axis z-z. An optical detector 14 is positioned ninety degrees away from source 13 for viewing the fluorescence trace 16 induced in the fiber/preform. Referring, for convenience, to the x-y-z coordinate system shown, the fiber/preform axis is aligned along the z-direction, the uv beam is directed along the x-direction, and the detector is located along the y-direction.

Figure 2:
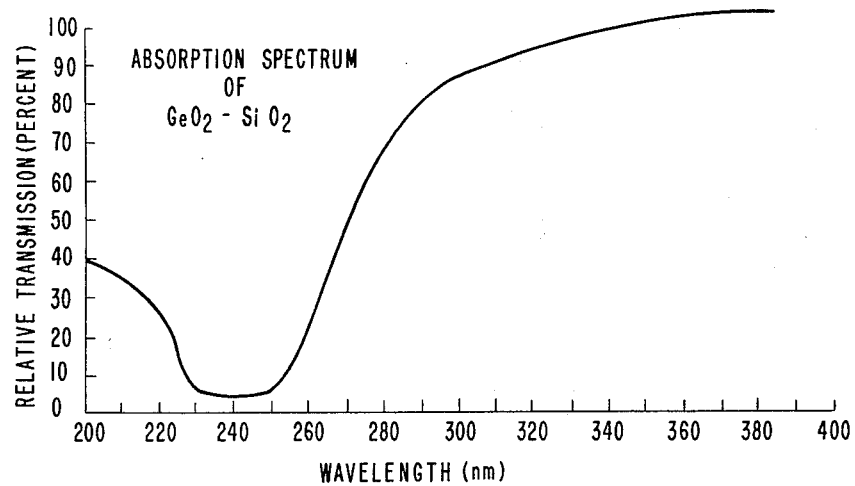
FIG. 2 shows the absorption spectrum of $GeO_2$-doped silica.

In a typical fiber/preform, the cladding material is made of undoped silicon dioxide (i.e., silica) which does not fluoresce when illuminated with uv radiation. The core region 11, however, contains an index-modifying dopant that absorbs uv radiation and fluoresces. For example, germanium doped silica fluoresces at a wavelength near 420 nm when excited by uv radiation at wavelengths below 350 nm. FIG. 2 shows the absorption spectrum of $GeO_2$-doped silica which exhibits a relatively broad absorption peak centered at 240 nm. For purposes of the present invention, a wavelength away from this peak is used so that the uv attenuation through the core is minimized. A preferred range of wavelengths for measuring germanium-doped cores is between 290 and 340 nm.

To confine the fluorescences to as thin a region of the core as possible, the uv is focused to a beam width, w, that is at least an order of magnitude less than the core diameter, d.

Having induced fluorescence along a diameter of the core, the intensity of the fluorescence is measured at points therealong by detector 14. The latter includes a photosensitive device, i.e., diode 15, an indicator 18, a focusing lens 16 and an aperture 17. The diode is located in the focal plane of lens 16 and is moved, along with aperture 17, in the x-direction so as to make point-by-point measurements of the intensity of the fluorescence along the trace 16. The resulting measurements are a direct indication of the index profile of the core as a function of the core radius.

Figure 3:
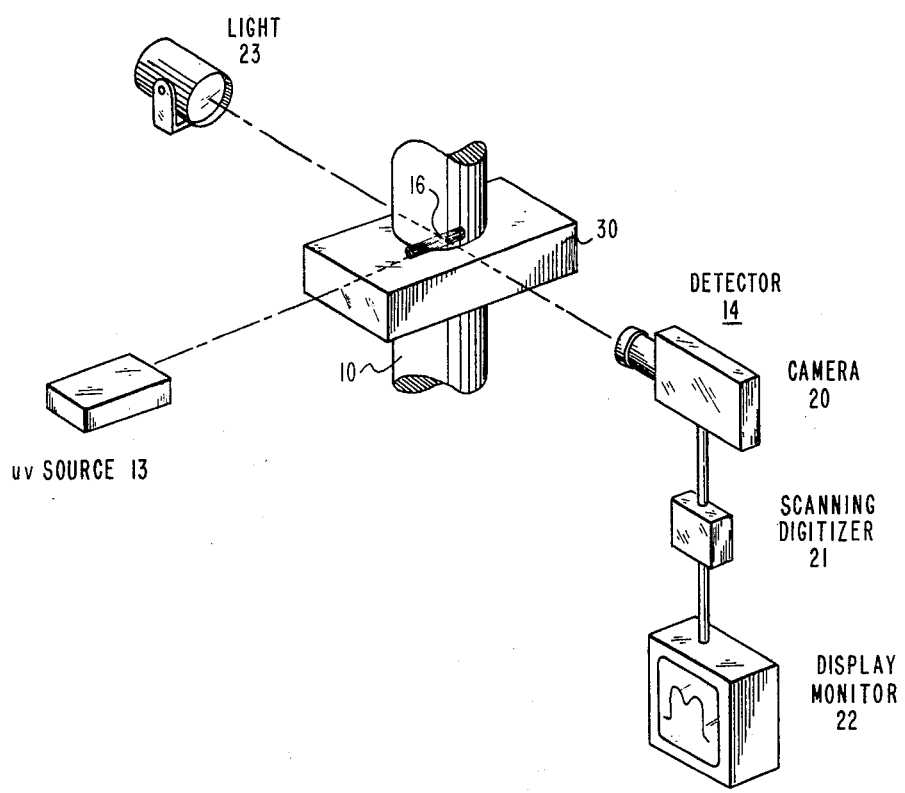
FIG. 3 shows alternate apparatus for practicing the invention.

In a more sophisticated arrangement, illustrated in FIG. 3, the detector 14 comprises a video camera 20, a scanning digitizer 21 and a display monitor 22. In operation, the camera is focused on the center plane of the core by back illuminating the fiber/preform by means of any convenient light source 23. If the camera is focused either behind or in front of the center of the core, the layered structure of the core is seen as alternating light and dark lines. When focused directly at the center, these structural features disappear and a uniformly illuminated image is observed.

Having focused the camera, light 23 is extinguished, and the uv source 13 is turned on. The scanning digitizer samples the induced trace, and generates electrical signals that are proportional to the measured intensities. These are transmitted to the display monitor for viewing.

In order to obtain the absolute value of the index profile, the arrangement is calibrated by measuring a sample having a known refractive index.

Figure 4:
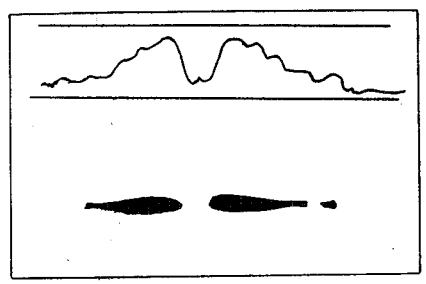
FIGS. 4, 5 and 6 show data obtained in accordance with the invention.
Figure 5:
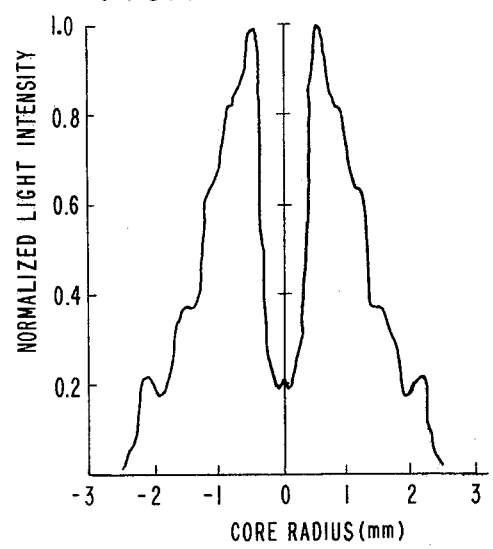

FIGS. 4 and 5 show data obtained from a specially prepared MCVD preform using the 325 nm wavelength output from a helium-cadmium laser focused by means of a 20 cm focal-length uv lens. FIG. 4 is a photograph of the display monitor. The upper curve is the intensity profile of the preform which has a multi-stepped $GeO_2$-doped core. When fabricated, the dopant concentration was increased in four steps. A final deposit of pure silica was then made to form the core center of the collapsed preform. The image below the curve is a picture of the fluorescing core which was about 5 mm in diameter.

FIG. 5 shows the resulting intensity profile after averaging ten scans to minimize the effects of spurious fluctuations of the uv laser. As can be seen, the individual regions of the core are clearly defined.

Figure 6:
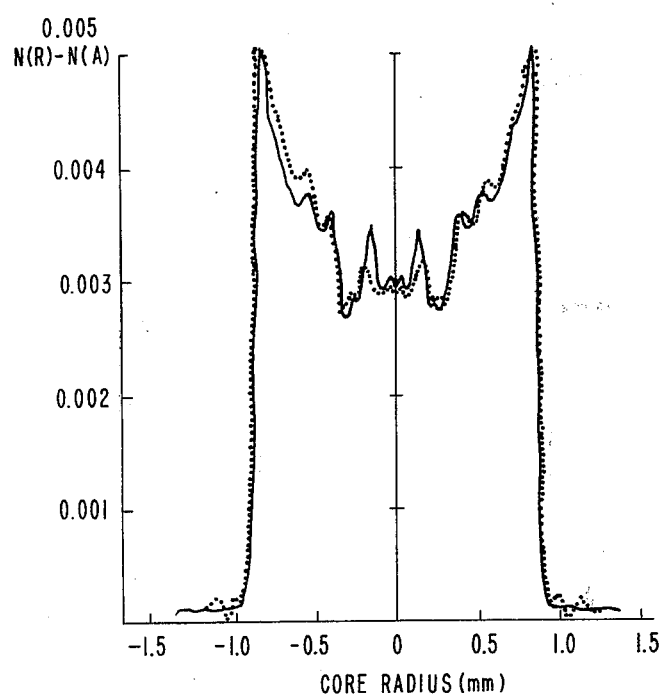

The above-described technique is equally applicable to single mode fibers and preforms having a step-index profile. FIG. 6 shows measurements made on a sample preform by the uv-fluorescence method, indicated by the solid curve, and by the focusing method described in U.S. Pat. No. 4,181,433, indicated by the dotted curve. The agreement between the two curves is seen to be very close.

As is known, the cylindrical cladding of a fiber/preform in air acts as a strong lens. This effect can be avoided by immersing the fiber/preform in an index-matching fluid 30, as shown in FIG. 3, and presenting perpendicular planar surfaces to the uv source and detector. In either case, the difference between using or not using index-matching only involves a scale factor and is important only if knowledge of the absolute core diameter is directly desired.

It was stated that the invention can be utilized with both fibers and preforms. In the former case, because of its smaller size, microscopes are used for focusing the incident uv and for observing the resulting fluorescence. Using conventional lasers, focused beams as small as 0.3 $\mu$m can be readily obtained. This is small enough for making observations in both the 50 $\mu$m cores of typical multimode fibers, and in the 5 to 10 $\mu$m cores of single mode fibers.

The above-described measuring technique can be used for real-time control of the fiber drawing process. For example, to insure single-mode propagation in a fiber, the core diameter, $2a$, and the relative index difference $\Delta = (n_1 - n_2)/n_1$ between the core of index $n_1$ and the surrounding cladding of index $n_2$ must be chosen so that the normalized frequency, $v$, is less than the cutoff frequency $v_c$. For the weakly guiding approximation, $\Delta << 1$, and for a uniform index distribution in the core, this condition is satisfied when $$v = \left(\frac{2\pi}{\lambda}\right) an_1 \sqrt{2\Delta} < 2.405. \tag{1}$$

Figure 7:
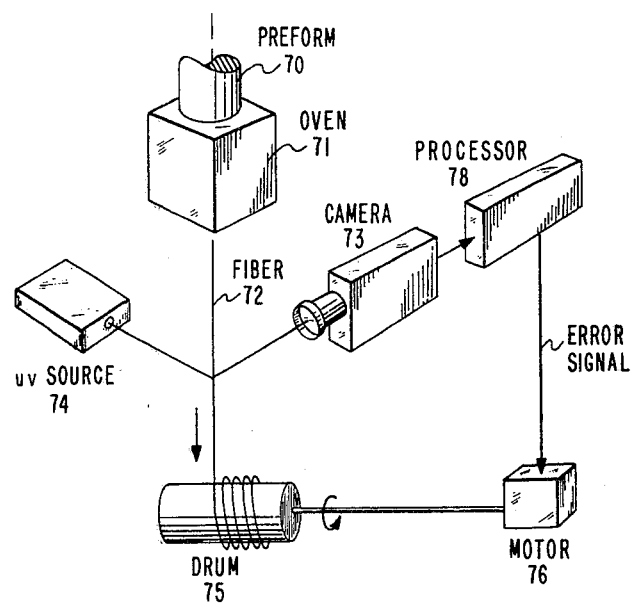
FIG. 7 shows an arrangement for controlling the fiber diameter as it is being drawn.

In practice the relative index difference, $\Delta$, is fixed during preform fabrication and the diameter of the core is adjusted during the pulling operation to satisfy the above relationship. However, local variations in either $\Delta$ or the core diameter can increase $v$ sufficiently so that it exceeds $v_c$. Accordingly, the index profile and fiber diameter are advantageously monitored as the fiber is being drawn, and the diameter varied, as required, so as to satisfy equation (1) at all times. An arrangement for doing this is illustrated in FIG. 7. As shown, a preform 70 is inserted in an oven 71 and a fiber 72 is drawn at a rate determined by a motor 76 driving a drum 75 under the control of a processor 78. As the fiber is being drawn, it is illuminated by uv source 74. The fluorescing core region is observed by a camera 73 and the intensity information thus recorded is fed to processor 78. The latter computes $\Delta$ and the core diameter and compares these values with previously stored information relating these parameters, as defined by equation (1). If the value of $\Delta$ is increasing, the processor causes the motor to rotate more quickly so as to reduce the fiber diameter. If, on the other hand, $\Delta$ is decreasing, the motor is caused to rotate more slowly. In either case, the result is to maintain single mode propagation in the fiber in the face of variations in the value of $\Delta$.

A more accurate method of measuring the core diameter, as disclosed in my copending application, Ser. No. 140,313, filed Apr. 14, 1980, can be used in conjunction with the present invention, if desired.

I claim:

1. A method of measuring an optical fiber/preform, comprising an inner core region containing an index-modifying dopant surrounded by an outer cladding, including the steps of:

illuminating a portion (16) of said fiber/preform with a beam (15) of ultraviolet radiation having a beam width at least an order of magnitude smaller than the diameter of said core region;

and measuring (14) the intensity of the fluorescence induced along said illuminated portion (16) by said ultraviolet radiation.

2. The method according to claim 1 wherein said beam is directed along the diameter of said fiber/preform.

3. The method according to claim 1 wherein said index-modifying dopant is germanium;

and wherein the wavelength of the ultraviolet radiation is within the range between 290 and 340 $\mu$m.

4. The method according to claim 1 wherein the illuminating beam is incident in a direction (x) normal to the longitudinal axis (z—z) of said fiber/preform.

5. The method according to claim 1 wherein the illuminated portion of said fiber/preform is immersed in an index-matching fluid.

6. A method of controlling the core diameter of an optical fiber as it is being drawn to assure single mode propagation including the steps of:

determining the index profile of said fiber (72) as it is being drawn by directing a beam of ultraviolet radiation having a width at least an order of magnitude smaller than said core along the diameter of said fiber and measuring the intensity of the fluorescence induced thereby;

comparing said intensity measurement with reference values to form error signals;

and varying the rate at which said fiber is drawn in response to said error signals.

* * * * *